United States Patent
Lautenschläger

[11] Patent Number: 5,981,924
[45] Date of Patent: Nov. 9, 1999

[54] METHOD AND APPARATUS FOR MEASURING PRESSURE IN MICROWAVE HEATED VESSELS

[75] Inventor: Werner Lautenschläger, Leutkirch, Germany

[73] Assignee: Milestone Inc., Monroe, Conn.

[21] Appl. No.: 08/932,301

[22] Filed: Sep. 17, 1997

[30] Foreign Application Priority Data

Sep. 23, 1996 [DE] Germany ............ 196 39 021

[51] Int. Cl.[6] .................................................. H05B 6/64
[52] U.S. Cl. ........................................................ 219/685
[58] Field of Search ............................ 219/686, 702, 219/704, 762, 709, 706

[56] References Cited

U.S. PATENT DOCUMENTS

| 4,693,867 | 9/1987 | Commarmot et al. | 422/62 |
| 5,424,717 | 6/1995 | Platt et al. | 340/551 |
| 5,429,799 | 7/1995 | Shieh et al. | 422/21 |

FOREIGN PATENT DOCUMENTS

| 4419648A1 | 9/1995 | Germany . |
| 4413425A1 | 10/1995 | Germany . |
| 63-150640 | 12/1986 | Japan . |
| 2 184 040 | 6/1987 | United Kingdom . |

OTHER PUBLICATIONS

Database WPI Section PQ, Week 9706.

*Primary Examiner*—Teresa Walberg
*Assistant Examiner*—Jeffrey Pwu
*Attorney, Agent, or Firm*—Fitzpatrick, Cella, Harper & Scinto

[57] ABSTRACT

A pressure monitoring system in which pressure in a container causes a slide which extends out from the container, to be moved against a group of springs in cascade formation and which are screened from microwave radiation. The extent of such movement, which corresponds to changes in container pressure, is measured by means of a light transmitter and a receiver which cause light to be reflected off a reflective surface of the slide and then analyzed. Also disclosed is a process in which the heating of a container is controlled as a function of the differential quotient of pressure over time.

23 Claims, 5 Drawing Sheets

METHOD AND APPARATUS FOR MEASURING PRESSURE IN MICROWAVE HEATED VESSELS

BACKGROUND OF THE INVENTION

1. Field of the Invention

The invention relates to a device and a process for treating a chemical substance by heating under pressure comprising at least one container which can be closed so as to be pressure-proof and serves to accommodate the substance.

Devices and processes of this type are used for example for the decomposition, elemental analysis or dehydration of sample material arranged in one or more container(s) by heating, the pressure in the containers increasing as a result of the heating.

DE 38 18 697 C2 has disclosed a heating device for heating sample material in pressure-proof sample containers composed of a housing and a cover. In this device the heating power is reduced as a function of the inner pressure in the container. The pressure indicator used for this purpose is formed by a slide which is displaceable via a membrane by the pressure in the container, and a pressure sensor or switch which is connected to a control circuit for the heating power of the heating device. Preferably, the heating device is formed by a microwave oven.

Furthermore, DE 39 19 601 C2 describes a device for the decomposition by acids of a substance for elemental analysis in a microwave field generated by a microwave oven under controlled pressure in a sealed decomposition vessel. In the device disclosed therein, which exclusively comprises parts made of microwave-permeable material, a microwave-permeable, measured value sensor on the one hand is actively connected to a pin whose vertical upwards movement is a gauge of the increase in pressure in the decomposition vessel, or is detachably connected thereto, and on the other hand is connected to a pressure display device or control device for the microwave heating arranged outside of the microwave oven. The microwave-permeable measured value sensors used are those which operate mechanically via a lever, hydraulically, pneumatically (in each case in contacting fashion) or optically (in non-contacting fashion).

The optical measured value sensor proposed in DE 39 19 601 C2 consists in the simplest example of an optical transmitter and a receiver, which latter receives the light beam emanating from the transmitter until the beam path is interrupted by the upwardly moving pin. The absence of the received signal then triggers the switching off of the microwave heating. Equally, a reflector can be arranged at the upper end of the pin so that upon the overshooting of a specified pressure, light is thrown back from the reflector onto the receiver and the microwave heating is thus switched off.

As in the described prior art all the parts must consist of microwave-permeable material, it is not possible to use elements which are actually more efficient, for example for sealing the container and for the pressure detection.

Additionally, the known pressure detection systems do not permit adequate control of the reactions occurring in the containers. In particular in processes for the decomposition of organic substances, extreme exothermic reactions take place which under normal circumstances go totally out of control and are associated with an extreme rise in pressure and temperature which frequently leads to the destruction of the containers. It is not possible to damp these reactions in association with normal pressure detection as, at the instant at which the energy supply is switched off, upon the overshooting of a predetermined pressure limit value in general a certain part of the sample material has already reacted and the reaction continues automatically and in an uncontrolled manner.

The aim of the invention is to provide a device of the type described in the introduction with an improved pressure monitoring system in which moreover more efficient components composed of microwave-absorbent material can be used.

Additionally, a process is to be provided which, by virtue of the pressure monitoring, facilitates improved control of the reaction occurring in the containers so that the reaction can be substantially prevented from going out of control and the reaction can be continued in controlled fashion at a constant pressure.

SUMMARY OF THE INVENTION

According to one aspect of the invention, this object is achieved by means of a microwave permeable, pressure container which is placed in microwave heater housing, a slide which is moveable relative to the container by pressure therein, and which reflects light from a light transmitter onto a light receiver, with the slide being so arranged relative to the light transmitter and receiver such that its movement changes the distance between a light reflecting surface thereon and at least one of the transmitter and receiver. The non-contacting, optical measured value recording of the distance between reflective surface and light transmitter and/or light receiver, which is changed as a function of the pressure in the container, permits continuous monitoring of the pressure and/or change in pressure in the container together with a high degree of accuracy.

According to a further aspect of the invention, there is provided a microwave permeable pressure container which is placed in a microwave heater along with a plurality of springs arranged inside a microwave screening cage to press a cover against the container. The construction of the pressure component from a plurality of springs made of spring steel and arranged one above another results in a displacement path of the cover which is virtually linearly proportional to the pressure over a wide displacement range, so that the displacement path of a slide connectible to the cover is also linearly proportional. To prevent heating of the spring arrangement, the latter must be screened from the microwave radiation, which is achieved by a specially designed metal cage functioning as Faraday cage for screening of the microwave radiation.

According to a still further aspect of the invention, there is provided a novel process for heating a substance under pressure which comprises the steps of applying heating power to a pressure container which contains the substance and, calculating a differential quotient of pressure within the container over time and interrupting the supply of heating power when the differential quotient exceeds a predetermined value. The differential quotient of change in pressure over time constitutes a considerably better controlled variable than simple pressure or temperature limit values as it indicates the onset of a reaction at an earlier instant of time with the result that the reaction can be damped promptly.

Further embodiments and further developments of the invention are also described herein.

BRIEF DESCRIPTION OF THE DRAWINGS

Exemplary embodiments of the device according to the invention and a process according to the invention will now be explained making reference to the attached drawing wherein.

DETAILED DESCRIPTION OF THE PREFERRED EMBODIMENTS

Figure 1:
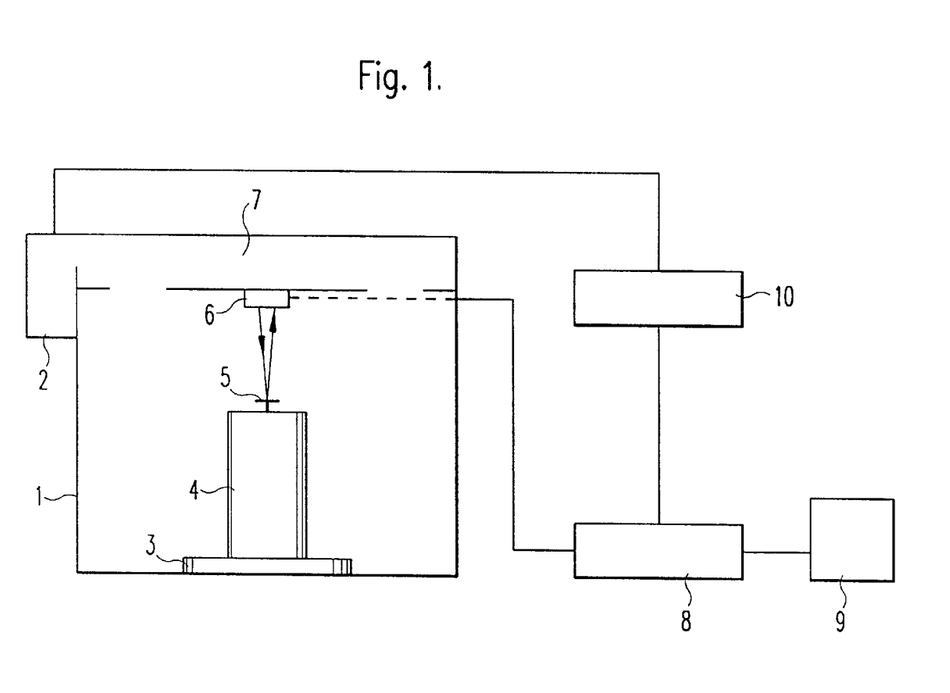
FIG. 1 shows a schematic diagram of a device according to the invention.

FIG. 1 schematically illustrates a device according to the invention. The device comprises a microwave oven with a microwave-screening housing 1, a microwave generator 2 and a means 7 for transmitting the microwaves from the microwave generator 2 into the interior of the housing 1. In the interior of the housing 1 a container arrangement 4, comprising a container which can be closed so as to be pressure-proof and serves to accommodate the substance, is arranged on a plate 3. On the upper side of the container arrangement 4 is arranged a slide 5 which serves as a pressure indicator and whose vertical position is a gauge of the pressure in the container and on whose upper side a reflector is arranged. Above the container arrangement 4 and the slide 5 in the interior of the housing 1 there is arranged an optical displacement sensor 6 comprising a light transmitter which transmits light directed towards the slide 5, and a light receiver which receives the light reflected by the reflector on the slide 5.

The optical displacement sensor 6 is connected to an analyzing unit 8 which is arranged outside of the housing 1 and which analyzes the reflected light received by the light receiver and determines the pressure and/or change in pressure in the container. The analyzing unit 8 is connected to an input- and output unit 9 via which the user can control and monitor the process. The analyzing unit 8 is further connected to a control circuit component 10 which is coupled to the microwave generator 2 for controlling the microwave power in accordance with the analyzed measurement results.

Figure 2:
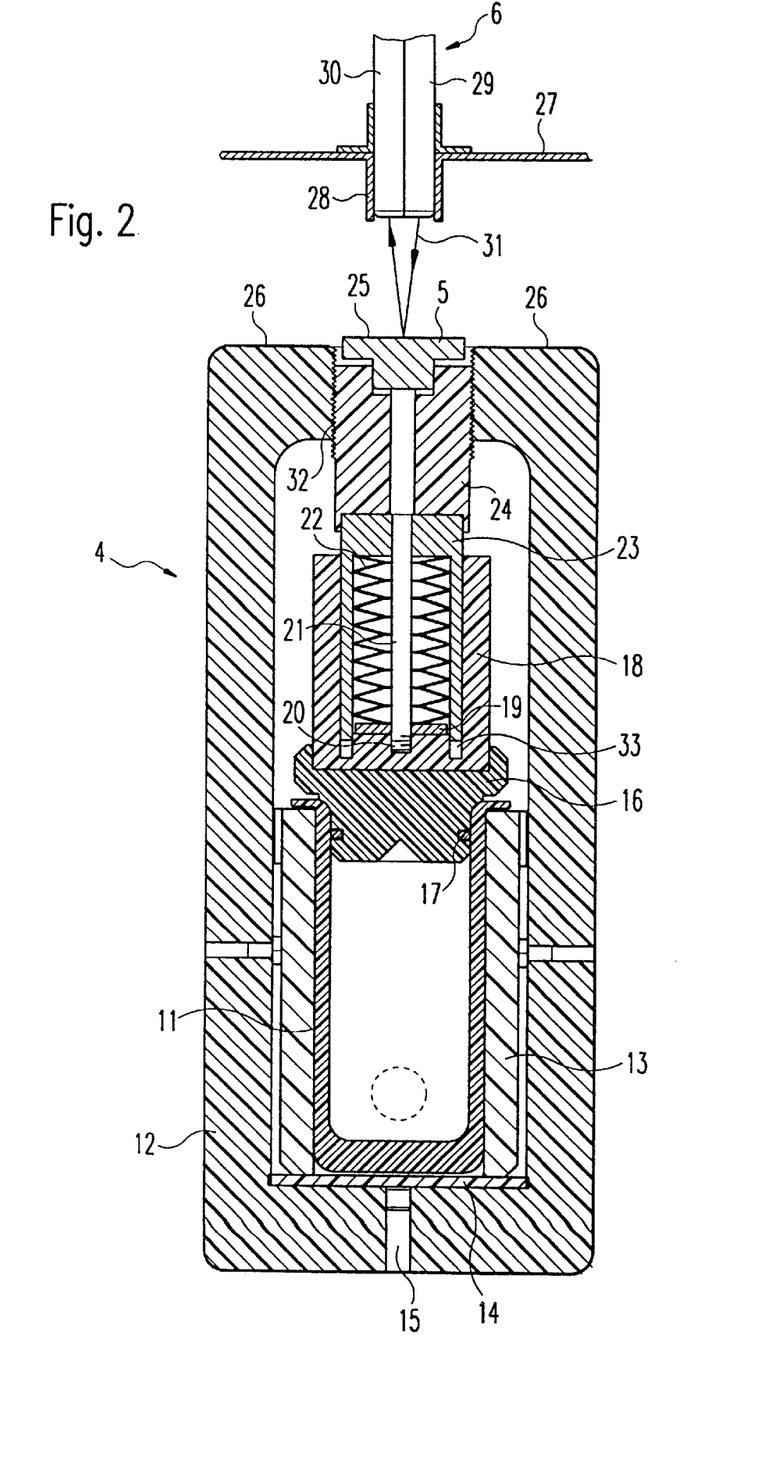
FIG. 2 shows a sectional diagram of an exemplary embodiment of a container arrangement according to the invention comprising pressure-tight container and pressure-detecting system.

FIG. 2 is a sectional diagram of the container arrangement 4 according to the invention comprising a container, which can be closed so as to be pressure-proof, and a pressure detecting system according to the invention. The cylindrical, upwardly open container 11 which serves to accommodate the substance is arranged in an outer container 12 and preferably produced from polytetrafluoroethylene (PTFE) or quartz. For thermal insulation, a sleeve 13 composed of high-temperature-compound plastic (HTC) is introduced between container 11 and outer container 12 and the container 11 is positioned on an insulating base plate 14. Below the container 11 and base plate 14 a through-opening 15 is provided in the outer container 12 as predetermined breaking point in the case of the explosion of the container 11 due to excessive inner pressure.

The container 11 is closed so as to be pressure-proof by a cylindrical cover 16 comprising a sealing ring 17. Like the container 11, the cover 16 is preferably made of PTFE.

An adapter component 18 for the coupling of the cover 16 and the pressure system described in the following is fixed to the cover 16. In the adapter component 18, which has the form of an upwardly open hollow cylinder, there is arranged a steel plate 19 which is centrally penetrated by a steel pin 21 whose lower end has a fixing thread 20 for attachment to the adapter component 18 and also serves as guide column for the cup springs 22.

Whereas all the previously described components 11–18 of the container arrangement 4 are to consist of a microwave-permeable material, in order not themselves to be heated by microwave radiation and not to impede the heating, by microwave radiation, of the substance arranged in the container 11, the cup springs 22 are made of spring steel. Spring steel ensures particularly good spring properties with regard to linear expansion even over relatively large displacement ranges. To intensify the property of linearity of expansion, a plurality of cup springs 22 are arranged one above another in a cascade formation.

However, the arrangement of the cup springs 22 consisting of spring steel in the microwave field has the disadvantage that they heat up. This is especially the case since their dimensions are in a specified ratio to the wavelength of the microwave radiation, but also in particular because the arrangement has corners and angles which act as antennae so that the microwaves penetrate into the metal and heat the latter. The heating can cause the cup springs to become red hot, with the result that their spring characteristic is permanently negatively affected and the linear expansion of the arrangement is no longer ensured.

To counter the last-mentioned negative effect, the cup springs 22 are surrounded by a cage 23. This cage 23 likewise consists of metal, preferably high-grade steel. However it is characterised by the fact that it has a polished surface and that the edges are rounded. Additionally, the dimensions of the cage 23, i.e. diameter and axial length, are preferably between a quarter of a wavelength and a whole wavelength of the microwave radiation used. Such a cage 23 is practically not heated by microwave radiation and serves as a Faraday cage in relation to the cup springs 22. Additionally, the surface of the metal cage 23 is preferably coated with a material, such as for example PTFE, which is resistant to aggressive chemicals in order to prevent the metal surface from being attacked by the chemicals.

The metal cage 23 is virtually a hollow cylinder with an open end side which is inverted over the cup spring arrangement. Externally it is guided in the adapter component 18 and internally it is guided by the metal pin 21, the upper end of said pin being guided through a central bore in the closed upper end side of the cage 23. As the closed end side of the metal cage 23 bears against the cup springs 22, the latter can be compressed by depression of the cage 23. For this purpose the adapter component 18 comprises corresponding recesses 33 for the accommodation of the depressed metal cage 23.

A pressure screw 24 is applied to the cage 23 in such a manner that its lower end face bears against the upper end face of the cage 23 so as to be rotationally moveable. The pressure screw 24 is guided by a continuous edge on the lower end side of the cage 23 so that the axis of rotation of the pressure screw 24 coincides with the longitudinal axis of the cylindrical cage 23.

The pressure screw 24 is introduced through a through-opening in the upper end side of the outer container 12 on whose inner side a thread 32 is provided, into which the pressure screw 24 engages. As a result of the screwing of the pressure screw 24 into the outer container 12, the metal cage 23 is depressed. The cup springs 22 transmit the force to the steel plate 19 and thus indirectly onto the adapter component 18 and the cover 16. As the steel pin 21, which is connected to the steel plate 19, is not held down by the cage 23 but is freely vertically moveable through the bore in the upper end face of the cage 23, the cover 16 on the container 11 also remains vertically freely moveable within specific limits. In accordance with the spring force of the cup spring arrangement, an equilibrium comes into being between the pressure applied by the pressure screw 24 in the downwards direction and the inner pressure in the container 11 in the upwards direction. As a result of the screwing of the pressure screw 24 into the outer container 12 at the start of the process, the pressure arrangement is prestressed. Here the cup springs 22 must be selected such that the inner container 11 remains closed in pressure-proof manner by the pressed-on cover 16 during the whole of the process.

The pressure screw 24 also has a central bore whose diameter corresponds at least to the diameter of the steel pin 21, so that the latter can extend through the upper end side of the cage 23 into the pressure screw 24 when the cover 16 is moved upwards as a result of the inner pressure in the container 11. A slide 5 is introduced into the bore of the pressure screw 24, the lower pin-like end of said slide 5 bearing against the steel pin 21 and the upper end of said slide being widened in excess of the diameter of the bore. The slide 5 is produced from a microwave-permeable material, such as for example plastics or ceramic. On the upper side of this widened portion the slide 5 has a reflective surface 25 which is aligned at right angles to the longitudinal axis of the slide 5 and the overall arrangement 4. The upper end side 26 of the outer container 12 is likewise reflective and aligned at right angles to the longitudinal axis of the overall arrangement 4 in order to be able to serve as reference surface. This reference surface 26 facilitates a more accurate detection of the pressure changes in the containers 11 as the exact (vertical) position of the container 11 in the housing 1 of the device is always taken into consideration and the measuring device 6 is thus self-adjusting.

The optical displacement sensor 6 is arranged above the container arrangement 4 on the top 27 of the microwave housing 1 in an extension of the longitudinal axis. It is surrounded by a metal pipe 28 which projects into the interior of the housing 1 and carries the same potential as the housing 1 so that the optical displacement sensor 6 is screened from the microwaves by the metal pipe 28.

Advantageously, a commercially available triangular-laser-diode sensor is used as optical displacement sensor 6. This sensor substantially comprises a light transmitter 29 which transmits light 31 directed towards the reflective surface 25 of the slide 5, and a light receiver 30 which receives the light 31 reflected by the slide 5. The triangular-laser-diode-sensor 6 is designed such that in the event of a change in the distance between reflective surface 25 and light transmitter 29 and/or light receiver 30, a change occurs in the angle of reflection of the light 31, and thus the intensity of the reflected light 31 received by the light receiver 30. This change in light intensity is converted into a change in the inner pressure in the container 11 by the analyzing unit 8 connected to the light receiver 30. Then, in accordance with the change in the inner pressure, the power of the microwave generator 2, and thus of the microwave radiation, is controlled via a control circuit component.

In place of the above described process of pressure detection using a triangular-laser-diode sensor 6, the change in the inner pressure in the container 11 can also be detected by a different means. For example, the change in the distance between reflective surface 25 and light transmitter 29 and/or light receiver 30 also results in a phase shift and in a change in the transit time of the reflected light 31. The changes in these two variables can also be detected using appropriate optical sensors 6 and converted into changes in the inner pressure.

In addition to detecting the inner pressure or change in pressure in the container 11, it is naturally also possible to measure and control the temperature in the container 11 using appropriate devices. As such devices form part of the general prior art and are not the subject of the present invention, they will not be discussed in detail here.

Figure 3:
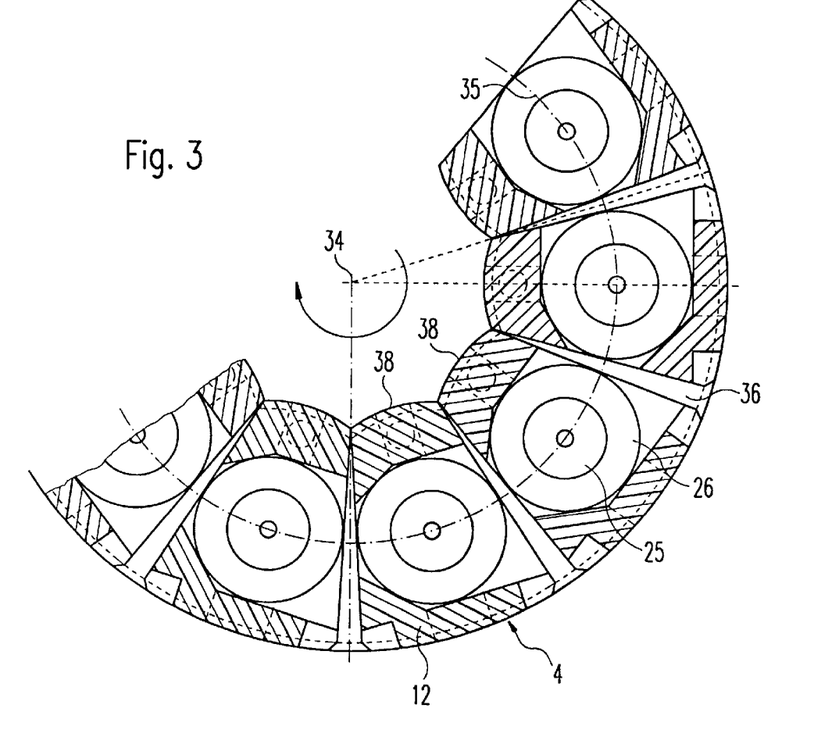
FIG. 3 shows a portion of a second exemplary embodiment of a device according to the invention in a plan view.

FIG. 3 illustrates another exemplary embodiment of the device according to the invention. Parts which have been explained with reference to the above exemplary embodiment have been identified by the same reference symbols in the following exemplary embodiment; their function will not be explained again.

In this example a plurality of container arrangements 4 are accommodated simultaneously in the microwave housing 1, so that a larger quantity of a chemical substance can be treated simultaneously with the device. FIG. 3 shows a portion of the arrangement of—in this case ten—container arrangements 4 in a plan view. The number of possible containers is basically unlimited, the upper limit being governed exclusively by the space requirement of the container arrangements 4 and the size of the housing 1.

The container arrangement 4 and outer forms of the outer containers 12 are segment-shaped, the construction of the container arrangements 4 corresponding to that explained with reference to FIG. 2. The segments 4 are arranged on a rotatable or pivotable, circular plate 3 so as to be symmetrical with respect to rotation about its centre point or axis of rotation 34.

Bores 38, to which an air cooling system is connectible, are also introduced in the end sides of the segments 4 facing towards the axis of rotation 34 of the plate 3. The inflowing air circulates round the sleeve 13 between container 11 and outer container 12 and thus prevents the excess heating of the container 11 during the reactions occurring in the chemical substance contained therein.

The pressure detection takes place on a circular path of revolution 35 formed by the longitudinal axes of the revolving arrangements 4 according to FIG. 2 and the revolving centre points of the reflective surfaces 25 of the individual slides 5. In order to be able to clearly separate the measured values of the individual segments 4 from one another, gaps 36 are provided between the reference surfaces 26 of the segments 4. The size of the reflective surfaces 25 and of the reference surfaces 26 are selected such that the response time of the sensor 6 is sufficient for the recording of the measured values.

Figure 4:
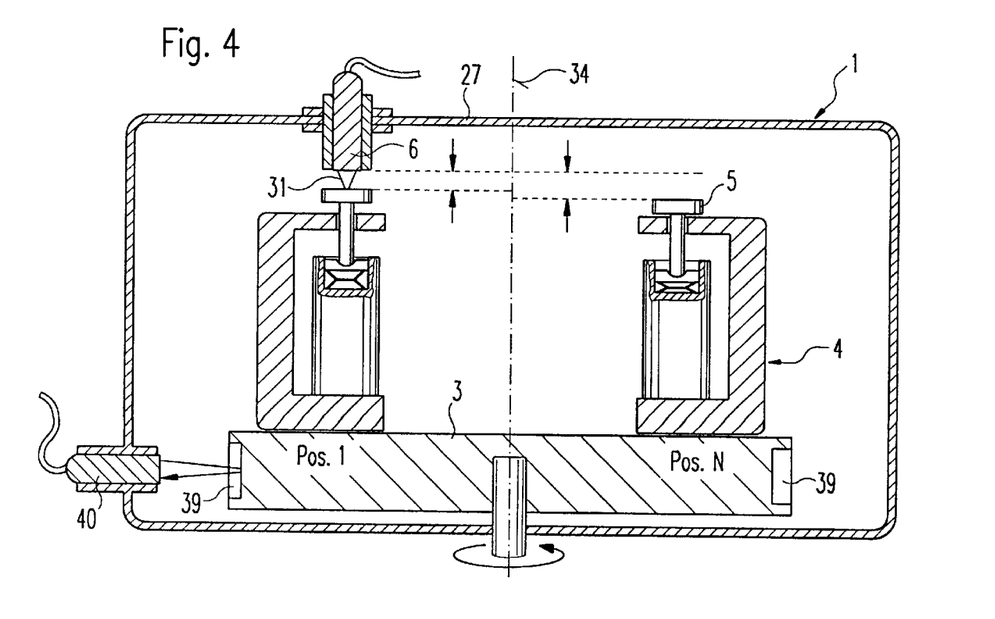
FIG. 4 shows the exemplary embodiment according to FIG. 3 in section.

As can be seen from FIG. 4, one single optical displacement sensor 6 on the top 27 of the microwave housing 1 is sufficient to detect the inner pressure in the containers 11. The optical displacement sensor 6 is situated at a location above the path of revolution 35 of the reflective surface centre points.

Figure 5:
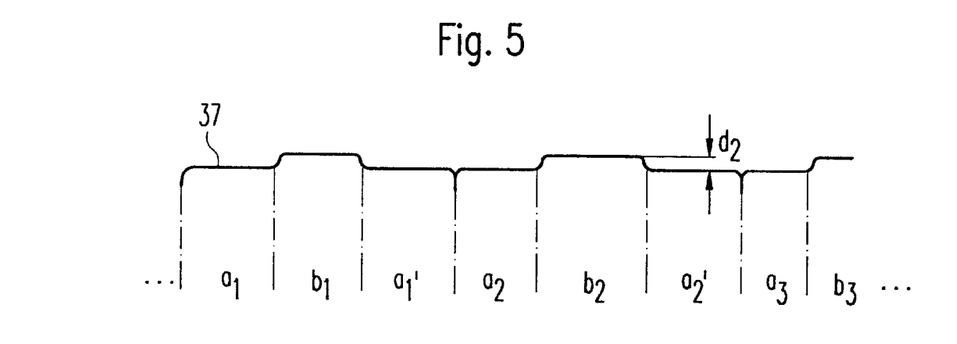
FIG. 5 shows a portion, serving by way of an example, of a measurement curve of the pressure-detecting system.

An example of a measurement curve 37 recorded by such an optical displacement sensor 6 is shown in part in FIG. 5 in which $a_1$ and $a_i'$ designate the measured value ranges in the regions of the reference surface 26 before and after the reflective surface 25 of the container arrangement No. i, and $b_1$ designates the measured value range in the region of the reflective surface 25 of container arrangement No. i. A pole position, which is produced by the gaps 36 between the segments and permits a clearly defined separation of the measured value ranges of the container arrangements No. i and No. i+1, in each case exists between the measured value ranges $a_i'$ and $a_{i+1}$. Here the index i extends from 1 to N, N being the number of segments 4 on the rotatable plate 3.

When the slide 5 of the segment No. i projects beyond the upper end side 26 of the outer container 12 of the corresponding segment 4, the optical displacement sensor 6 records a difference in level $d_i$ between the reflective surface 25 and the reference surface 26 of the container arrangement No. i. The pressure change in the container 11 of segment No. i is determined from the difference in the level differences $d_i$ between two revolutions of the rotor rotation, the spring constants of the cup springs 22 being included in particular in the calculation.

As can be seen from FIG. 4, the change in pressure need not amount to the same value in all the segments 4; rather, due to different inner pressures in the containers 11, the slides 5 can project by different amounts beyond the reference surfaces 26. The control of the microwave power by the analyzing unit 8 will in general take place as a result of the greatest occurring pressure change. The rotation of the plate 3, and thus of the segments 4, must take place sufficiently fast to ensure that the pauses between two measured values of a segment are not too great and on the other hand should not take place too fast to ensure that the response time of the optical displacement sensor 6 is adequate, with corresponding dimensions of the reflective- and reference surfaces 25 and 26. For this purpose, for example the rotational speed of the plate 3 can amount to approximately 10–20 revolutions per minute, which corresponds to a measurement interval of approximately 3–6 seconds, and the diameter of the reflective surface 25 can amount to approximately 30 to 40 mm.

A general problem in the detection of the container arrangements 4 in a rotating system resides in the coding of the individual positions. For this purpose, the automatic distance sensing used for the pressure measurement can also be employed in different ways for the coding of the container arrangements 4. Here it is possible either to code only one of the container arrangements 4, for example as container No. 1, or however to provide an absolute coding on all the container arrangements 4. The coding is required for the assignment of the measurement results to the pressure changes and for automatic removal by robot.

For the purpose of the coding, coded bores 39 are in each case provided in the rotatable plate 3 at the positions below the segments 4. The shape of the bores 39 is fundamentally arbitrary. However, a reflective surface in the bore 39 and a different depth of all the bores 39 are crucial. At the level of the bores 39 of the plate 3, a coding detector 40, whose construction and mode of functioning correspond to the above explained optical displacement sensor 6, is arranged at a location of the microwave housing 1. Instead of being arranged in the plate 3, the coding bores 39 can also be provided in the segments 4 themselves, with a correspondingly higher positioned coding detector 40.

Figure 6:
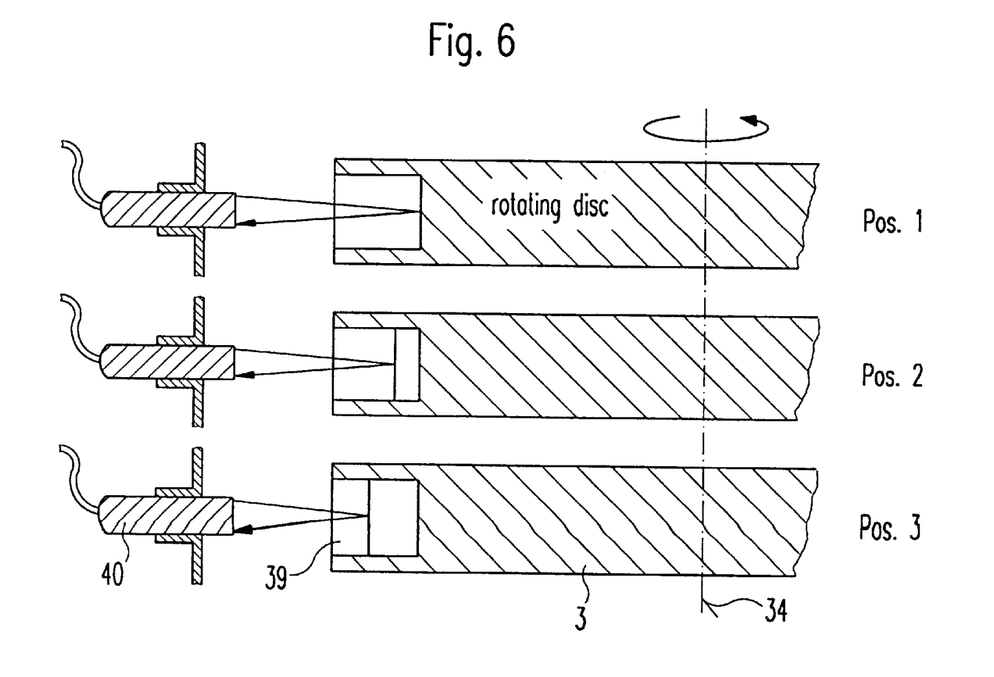
FIG. 6 shows an enlargement of a portion of FIG. 4.

The mode of functioning of the coding will now be explained in detail making reference to FIG. 6. The positions of three segments 4 have been shown one below another, while for clarity only the portions of the plate 3 and the coding detector 40 have been shown. The coding bores 39 of the three positions have a different depth, with the result that the positions can be clearly differentiated from one another. Prior to the start of a reaction, the stepped bore depth is recorded together with the respective measured value of the slide position and later used as absolute coding of the individual container arrangements 4.

An alternative means of coding consists in that all the bores 39 are formed with the same depth and the signals detected by the detector 40 serve merely as control signals for the optical displacement sensor 6 and indicate that a container is in the measuring position. In this case a substantially simpler and thus cheaper detector can be used. In order nevertheless to obtain a coding of the container arrangements 4, for example the container arrangement No. 1 is oriented at a significantly higher level than the other container arrangements Nos. 2 to N.

Finally the mode of functioning of the process according to the invention, in which the reactions in the containers 11 can be substantially prevented from going out of control, will be explained with reference to a pressure-time diagram, shown by way of an example in FIG. 7.

In the illustrated diagram the pressure P in the range of 0–10 MPa (0–100 bar) is plotted at the top and the time t in the range of 0–30 mins is plotted on the right. The strip above the pressure-time diagram indicates the power of the microwave generator 2 in watts during the respective time interval.

In contrast to previously known processes, instead of a simple pressure- or temperature limit value a limit value of the differential factor, pressure change over time, is used as controlled variable for controlling the microwave power. The input of simple pressure- or temperature limit values does not permit a sufficiently reliable control as reactions commence at different values depending upon the structure of the substance. If, upon the switching off of the microwave power, a relatively large part of the sample has already reacted, the reaction automatically goes out of control and generates an extremely high pressure in the container 11. This situation is indicated in the diagram by the broken-line curve 41.

Figure 7:
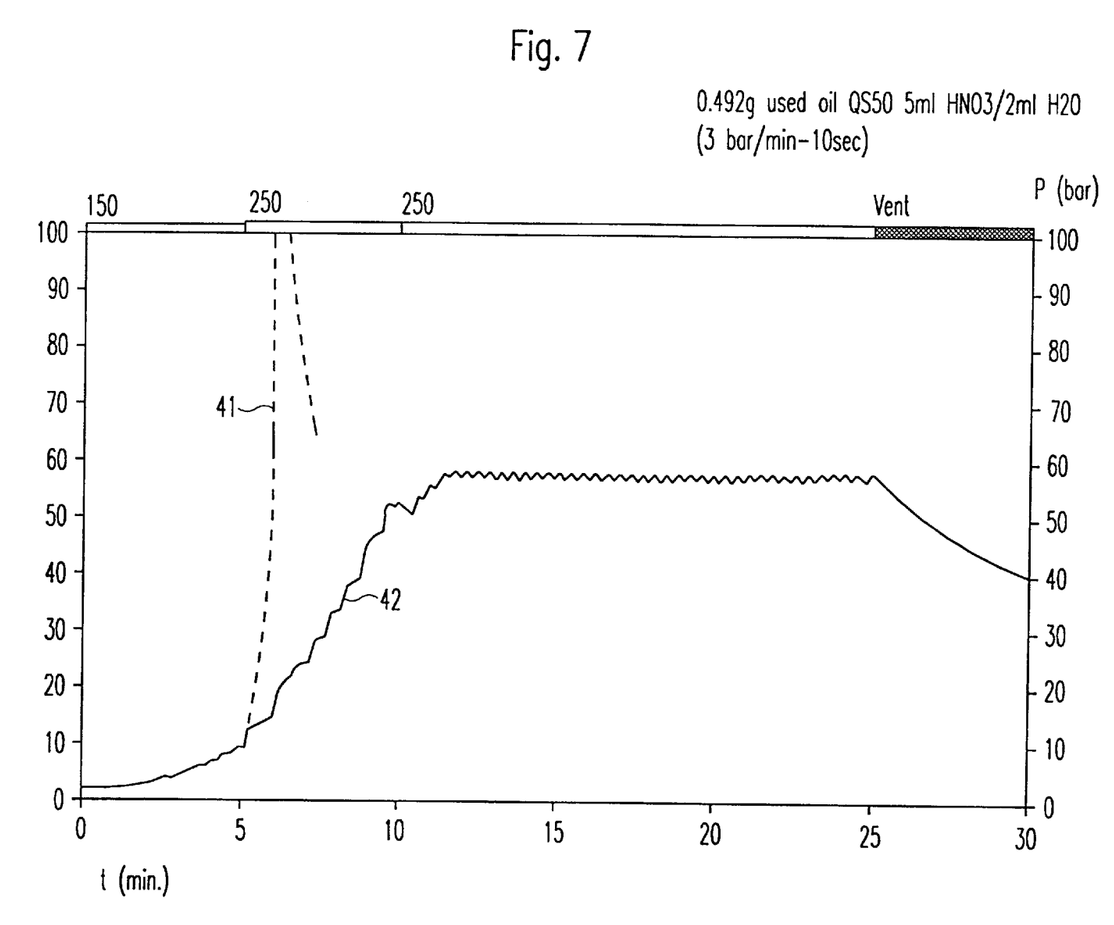
FIG. 7 shows a pressure-time diagram in explanation of the process according to the invention.

The solid-line curve 42 in the diagram in FIG. 7 shows, by way of an example, the controlled reaction of a weighed portion of approximately 0.5 g used oil with a predetermined limit value of the controlled variable of 0.3 MPa/min (3 bar/min) and a measurement interval of 10 seconds. During the first 5 minutes the reaction is kept under control by switching on and off the microwave radiation power of 150 watt in stages, so that the pressure change does not exceed the limit value of 0.3 MPa/min (3 bar/min). The reaction is controlled in the same way during the next 5 minutes with a microwave power of 250 watt. Then the pressure is maintained constant for 15 minutes at approximately 6 MPa (60 bar) by switching on and off at 250 watt. Then the cooling commences with the microwave radiation switched off. The use of microwave radiation is particularly advantageous for an accurate and reliable control of the reactions in the containers 11 as the energy supply can immediately be regulated or stopped by respectively regulating or switching off the microwave generator 2.

The process described with reference to FIG. 7 is fundamentally independent of the type of pressure measurement used.

I claim:

1. A device for treating a chemical substance by heating under pressure, comprising a housing which impedes the passage of microwave radiation, a microwave source connected to the interior of the housing, at least one container made of micro-wave-permeable material which can be closed so as to be pressure-proof and which serves to accommodate the substance, a slide which is adjustable by the pressure in the container and which has a reflective surface, a light transmitter which transmits light which is directed towards the slide and is reflected by the slide, a light receiver which receives and analyzes the reflected light, and a control circuit component, connected to the light receiver, for the microwave source, wherein the light transmitter, the light receiver and the reflective surface of the slide are positioned with respect to each other, wherein as a result of a change in the slide position the reflective surface causes a change in at least one of phase shift, transit time and angle, of reflected light received by the light receiver as the distance of the reflective surface from the light transmitter or light receiver is changed.

2. A device as claimed in claim 1, wherein as a result of the change in the angle of reflection, the intensity of the light received by the light receiver is changed and a change in pressure in the container can be detected from this change in intensity.

3. A device as claimed in claim 1, wherein light transmitter and light receiver are surrounded by a screen which carries the same potential as the housing in order to be screened from the microwave radiation.

4. A device as claimed in claim 1, wherein light transmitter and light receiver project into the interior of the housing in order to reduce the distance between themselves and the reflective surface.

5. A device for treating a chemical substance by heating under pressure, comprising a housing which impedes the passage of microwave radiation, a microwave source connected to the interior of the housing, at least one container made of microwave-permeable material which can be closed by a cover so as to be pressure-proof and which serves to accommodate the substance, and a spring pressure arrangement which serves to press the cover against the container, wherein the pressure arrangement contains a plurality of springs arranged one above another in an axial direction and the spring arrangement is surrounded by a cage for screening from microwave radiation in order to prevent heating of the spring arrangement by the microwave radiation.

6. A device as claimed in claim 5, wherein the cage is made of metal and its dimensions in relation to the wavelength of the microwave radiation are selected such that it is not heated by the microwaves.

7. A device as claimed in claim 5 wherein the surface of the cage is polished.

8. A device as claimed in claim 6 wherein the cage forms a hollow cylinder with a closed end wall whose diameter and axial length in each case amount approximately to between a quarter of a wavelength and a whole wavelength of the microwaves.

9. A device as claimed in claim 5 wherein the outer surface of the cage is polished.

10. A device as claimed in claim 5 wherein the edges of the cage are rounded.

11. A device as claimed in claim 5 wherein the surface of the cage is coated with a material which is resistant to chemical action.

12. A device as claimed in claim 5 wherein a pressure indicator is provided which analyzes the position of the cover on the container, which position can be changed by the pressure in the container.

13. A device as claimed in claim 5 wherein the pressure indicator consists of a slide, which is displaceable by the pressure in the container, and a sensor unit.

14. A device for treating a chemical substance by heating under pressure, comprising a housing which impedes the passage of microwave radiation, a microwave source connected to the interior of the housing, at least one container made of microwave-permeable material which can be closed by a cover so as to be pressure-proof and which serves to accommodate the substance, and a spring pressure arrangement which serves to press the cover against the container, wherein the pressure arrangement contains a plurality of springs arranged one above another in an axial direction and the spring arrangement is surrounded by a cage for screening from microwave radiation in order to prevent heating of the spring arrangement by the microwave radiation, a pressure indicator which analyzes the position of the cover on the container, which position can be changed by the pressure in the container, said pressure indicator comprising a slide which is displaceable by the pressure in the container, and a sensor unit, said pressure indicator being designed in accordance with one of claims 1 to 4.

15. A device as claimed in claim 5 wherein a plurality of containers are arranged in the housing on a rotatable or pivotable plate in order to treat a plurality of containers simultaneously.

16. A device as claimed in claim 15 wherein only one sensor unit is provided for detecting the pressure changes in the containers.

17. A device as claimed in claim 15 wherein a coding device is provided for coding the positions of the containers on the plate.

18. A device as claimed in claim 17 wherein the coding device consists of a coding detector and bores, in each case of different depth, at the positions of the containers in the plate or in the containers.

19. A device as claimed in claim 18 wherein the coding detector is a sensor unit having the same construction and mode of functioning as that of the pressure indicator, and the bores have reflective surfaces.

20. A process for treating a chemical substance by heating under pressure in which the substage is heated in a closeable pressure proof container, in which the pressure in the container is measured over a specified time period by measuring the position of a slide which is adjustable by the pressure in the container, said slide having a reflective surface which reflects from a transmitter back to a light receiver which receives and analyzes the reflected light, and in which the supply of heating power to the container is controlled as a function of the measured value, wherein the differential quotient of pressure over time is calculated and the supply of heating power is interrupted when the differential quotient exceeds a specified maximum value.

21. A process as claimed in claim 20 wherein microwave radiation is used for heating the substance in the containers.

22. A process as claimed in claim 20 wherein the differential quotient is calculated by means of a pressure indicator in accordance with the device claimed in one of claims 1 to 16 and 18 to 22.

23. A device according to claim 5, wherein said springs comprise metallic cup springs in a cascade formation.

* * * * *